(12) United States Patent
Galperin

(10) Patent No.: US 6,941,323 B1
(45) Date of Patent: Sep. 6, 2005

(54) SYSTEM AND METHOD FOR IMAGE COMPARISON AND RETRIEVAL BY ENHANCING, DEFINING, AND PARAMETERIZING OBJECTS IN IMAGES

(75) Inventor: Michael Galperin, Escondido, CA (US)

(73) Assignee: Almen Laboratories, Inc., Escondido, CA (US)

( * ) Notice: Subject to any disclaimer, the term of this patent is extended or adjusted under 35 U.S.C. 154(b) by 0 days.

(21) Appl. No.: 09/370,366

(22) Filed: Aug. 9, 1999

(51) Int. Cl.⁷ ............................................. G06F 17/30
(52) U.S. Cl. ......................... 707/104.1; 707/3; 707/6; 382/260; 382/130
(58) Field of Search .................. 707/104.1, 3; 382/305, 382/260, 168, 128, 130, 132

(56) References Cited

U.S. PATENT DOCUMENTS

| | | | |
|---|---|---|---|
| 5,019,975 A | | 5/1991 | Mukai |
| 5,568,384 A | | 10/1996 | Robb et al. |
| 5,579,471 A | | 11/1996 | Barber et al. |
| 5,586,197 A | | 12/1996 | Tsujimura et al. |
| 5,640,462 A | | 6/1997 | Sato et al. |
| 5,644,765 A | * | 7/1997 | Shimura et al. ............ 395/615 |
| 5,659,626 A | * | 8/1997 | Ort et al. .................... 382/125 |
| 5,684,999 A | | 11/1997 | Okamoto |
| 5,708,805 A | | 1/1998 | Okamoto et al. |
| 5,748,173 A | | 5/1998 | Gur |
| 5,787,419 A | | 7/1998 | Sato et al. |
| 5,802,361 A | * | 9/1998 | Wang et al. ................. 395/600 |
| 5,819,288 A | | 10/1998 | De Bonet |
| 5,835,619 A | | 11/1998 | Morimoto et al. |
| 5,852,823 A | | 12/1998 | De Bonet |
| 5,857,199 A | * | 1/1999 | Tamano et al. ............. 707/104 |
| 5,893,095 A | | 4/1999 | Jain et al. ....................... 707/6 |
| 5,911,139 A | * | 6/1999 | Jain et al. ....................... 707/3 |
| 5,930,783 A | | 7/1999 | Li et al. ........................... 17/3 |
| 5,984,870 A | | 11/1999 | Giger et al. .................. 600/443 |
| 5,987,094 A | * | 11/1999 | Clarke et al. .................. 378/62 |
| 6,011,862 A | * | 1/2000 | Doi et al. ..................... 382/132 |
| 6,012,069 A | * | 1/2000 | Shibazaki .................... 707/104 |
| 6,018,586 A | * | 1/2000 | Kamei ......................... 382/125 |
| 6,032,157 A | * | 2/2000 | Tamano et al. ............. 707/104 |
| 6,067,373 A | * | 5/2000 | Ishida et al. ................. 382/130 |
| 6,072,904 A | * | 6/2000 | Desai et al. ................. 382/225 |
| 6,181,817 B1 | * | 1/2001 | Zahib et al. ................. 382/170 |
| 6,226,636 B1 | * | 5/2001 | Abdel-Mottaled et al. ..... 707/4 |
| 6,240,423 B1 | * | 5/2001 | Hirata ......................... 707/104 |
| 6,310,967 B1 | * | 10/2001 | Heine et al. ................. 382/128 |

FOREIGN PATENT DOCUMENTS

| | | | |
|---|---|---|---|
| WO | 99/34319 | 7/1999 | ............ G06K/9/00 |
| WO | 00/43910 | 7/2000 | ............. G06F/9/00 |

OTHER PUBLICATIONS

Flickner et al. "Query by Image and Video Content: The QBIC System" Computer , vol.: 28 Issue: 9 , Sep. 1995 Page(s): 23 –32.*

(Continued)

Primary Examiner—Jean R. Homere
Assistant Examiner—Khanh Pham
(74) Attorney, Agent, or Firm—Knobbe Martens Olson & Bear LLP

(57) ABSTRACT

An image comparison and retrieval system compares objects and object clusters, or images. User controlled or automatic filtering to enhance object features is performed, and object pixels are defined. An object characterization parameter is computed based on certain object pixel values that characterize one or more aspects of the defined object. Object characterization parameters are compared for objects in different images to produce a measure of object similarity in the same or different images. The query image may be substantially continuously displayed during the image filtering and object definition processes.

14 Claims, 9 Drawing Sheets

OTHER PUBLICATIONS

Lee et al. "Query by Image Content Using Multiple Object and Multiple Features: User Interface Issues" Image Processing, 1994. Page(s): 76 –80 vol. 2.*

Hirata et al. "Object–based Navigation: an Intuitive Navigation Style for Content–oriented Integration Environment", Proceedings of the eighth ACM conference on Hypertext Apr. 1997, pp. 75–86.*

Hirata et al. "Media–Based Navigation for Hypermedia System" Proceedings of the fifth ACM conference on Hypertext Dec. 1993, pp. 159–173.*

Giordan et al, "Using Adobe Photoshop 5", Que Publisher, Jun. 1998, 600pp.*

Bimbo, et al., Image Description and Retrieval, E. Vicario ed., Chapter 7, pp. 161–191, Copyright 1998, "Using Weighted Spatial Relationships in retrieval by Visual Contents.".

* cited by examiner

SYSTEM AND METHOD FOR IMAGE COMPARISON AND RETRIEVAL BY ENHANCING, DEFINING, AND PARAMETERIZING OBJECTS IN IMAGES

BACKGROUND OF THE INVENTION

1. Field of the Invention

The invention relates to management of an image database and the retrieval of images therefrom.

2. Description of the Related Technology

The ability to search image databases and retrieve images therefrom with desired features or characteristics is important in many different environments. However, as a collection of images to be searched grows in size, the ability to search the collection manually for images having the desired features becomes increasingly limited. It can be appreciated that huge image databases of thousands or even millions of images have been created which are essentially impossible to search manually.

Several approaches have been used to automate the image search process. In some cases, images are digitized and stored in a database in association with one or more keywords which describe their content or character. Such a database can be searched linguistically for particular keywords, and images which are associated with these keywords are retrieved in response.

In a more recently developed alternative method, one or more "query images" are utilized, and images from the database which are in some sense similar to the query image are located and retrieved. In these systems, the pixel values of the query image and the images in the database are processed to produce a set of parameters indicative of color distribution, pixel intensity variation across the image, as well as other characteristics of the image as a whole. These parameters are calculated using various image filtering and processing techniques so as to produce a vector of feature parameters which is indicative of the image itself. The comparison process involves comparing feature vectors from images in the database with a query feature vector, and images from the database having similar feature vectors are retrieved. A system of this nature is described in U.S. Pat. No. 5,644,765 to Shimura et al., the disclosure of which is hereby incorporated by reference in its entirety.

The above described systems have several limitations. The most serious drawback for both cases is that image content is inadequately defined, which impacts both system recall and precision. Recall is the proportion of relevant images in the database that are retrieved, and precision is the proportion of retrieved documents that are actually relevant. These two measures may be traded off one for the other, and the goal of image retrieval is to maximize them both.

SUMMARY

The invention comprises methods and systems for processing, comparing and retrieving images. In one embodiment, the invention comprises a method of identifying similarities between first and second imaged structures present in one or more digital images. The method includes processing one or more digital images so as to define at least first and second objects, assigning a first object characterization parameter set to the first object, and assigning a second object characterization parameter set to the second object. The method further comprises calculating a similarity index based on the first object characterization parameter set and the second object characterization parameter set.

In another embodiment, the invention comprises a method of retrieving digital images having content similar to the content of a query image. In this embodiment, the invention comprises filtering a query image with a modifiable filtering function to produce a user selected filtered query image, substantially continuously displaying the filtered query image as the filtering function is applied to produce the filtered query image, comparing at least a portion of the filtered query image to at least portions of images in an image database, and selecting one or more images in the image database or portions thereof which are similar to the at least a portion of the filtered query image.

Image retrieval systems are also provided. In one embodiment such a system comprises an image database comprising a plurality of images, at least one query image stored in a memory, and a user definable filter set receiving both the query image and receiving images from the image database as inputs. The filter set is configured to provide a filtered query image and filtered database images as outputs to an object definition module in data communication with the filter. The object definition module is configured to define objects within the filtered query image and the filtered database images. The system also includes an object parameterization module configured to calculate a parameter set associated with at least one object in the filtered query image and a parameter set associated with at least one object in the filtered database images. A parameter set comparison module receives the parameter sets as inputs, and is configured to compare the content of the parameter sets.

Another system in accordance with the invention includes an image filter having a raw image as an input and a filtered image as an output and an image display device receiving the filtered image output from the image filter. An input device provides input parameters for modifying a filtering function performed by the image filter, whereby an image appearing on the image display device is updated substantially continuously as the filtering function is modified. In this embodiment, the system also includes a database of images and an image comparison module configured to compare the filtered image output with images in the database and to select images in the database which are similar to the filtered image output. Filtering and enhancement processes can be automatic and use system calculated default parameters.

In another embodiment, the comparison process is weighted. Thus, a method of comparing an object in a query image with objects in images in an image database comprises defining a plurality of parameters characterizing the objects, calculating a parameter vector comprising said plurality of parameters for objects in the image database so as to produce a set of parameter vectors, deriving a set of weights from the calculated set of parameter vectors, wherein each weight is associated with a corresponding one of the plurality of parameters. A parameter vector comprising the plurality of parameters for an object in said query image is calculated, and a weighted comparison between the object in the query image and the objects in the image database using the parameter vectors and the derived weights is performed.

DETAILED DESCRIPTION OF THE INVENTION

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

In many imaging applications, a user of the system wishes to find images in an image database which contain a certain defined object. In some cases, the search may be for images containing a chair, sunset, mountain, or the like. This may be the case in the advertising or commercial arts fields, for example, where large searchable image files are kept for use in the production of artwork, posters, etc. Other applications may also benefit from a robust object recognition system. In the health care environment, images such as X-ray films, CAT scans, and MRI images generally contain specific internal objects of interest such as blocked blood vessels, tumors, and other structures. In many cases, diagnosis and treatment would be facilitated if a physician could search an image database for similar structures found in other patients so as to obtain valuable information regarding diagnosis, treatment, and outcome for other patients showing similar objects under X-ray or MRI imaging. As yet another example, geographical and geological surveying, mapping, and other forms of reconnaissance would also be facilitated by such a system. Structures in aerial and satellite photographs could more easily be correlated to specific physical objects if specific ambiguous structures in the image could be cross referenced to structures found in other aerial or satellite photographs. To address this need, embodiments of the invention allow a user to focus image database searching on objects contained in an image. This dramatically improves the ability of the system to quickly and accurately identify desired images over the methods currently available in the technology and industry.

Figure 1:
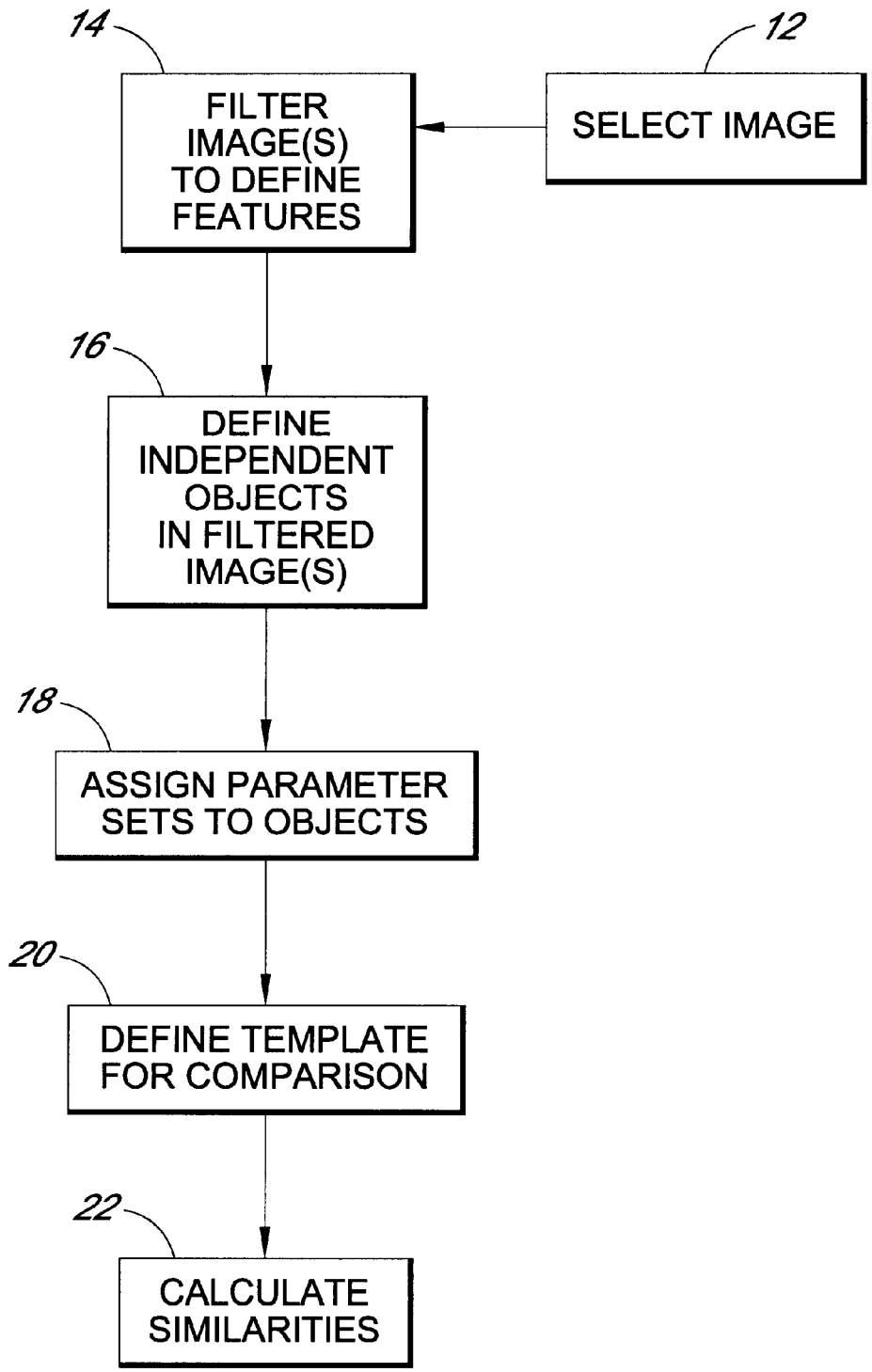
FIG. 1 is a flowchart of a method of image retrieval in one embodiment of the invention.

Referring now to the flowchart of FIG. 1, a method of image comparison according to one embodiment of the method begins at block 12, where a starting or query image is selected. The query image will typically be provided by a user of the system and will comprise an image which contains one or more structures or objects of interest. Initially, the structure of interest in the image may not be well defined or distinct relative to the background. For example, the object boundaries may be poorly delineated, or it may have significant internal features present that are not immediately apparent in the image.

To help define the object of interest, both in terms of its boundaries and its internal features, the system performs image filtering at block 14. In advantageous embodiments, the filtering performed is under the control of the system user. The system may also perform filtering automatically using default filter functions or filter functions previously defined and stored by a user. A wide variety of well known image filtering techniques may be made available to the user. Many image filtering techniques which may be used in embodiments of the invention are described at pages 151–346 of *The Image Processing Handbook,* 2d Edition, John C. Russ, author, and published in 1995 by CRC Press, which is hereby incorporated by reference into this application in its entirety. Several filters which are utilized in one embodiment of the invention are set forth below with reference to FIGS. 4–6. These filters may enhance edges, enhance the appearance of pixels in particular brightness ranges, stretch contrast in selected pixel brightness ranges, reduce noise, or perform any of a wide variety of pixel processing functions. It will be appreciated that the filtering performed at block 14 may comprise the sequential application of several individual pixel filtering functions. Advantageously, filtering performed in block 14 can result in the enhancement of features which are characteristic of objects of interest or objects within a certain class, etc., but which do not appear in other objects or in the image background.

Following the filtering of block 14, objects within the filtered image are defined at block 16. Once again, this process may be performed under the control of the user, or performed automatically by the system. In general, this process involves evaluating pixel values so as to classify them as either an object pixel or a background pixel. As with the filtering performed at block 14, the object definition process of block 16 may be done using many well known techniques, some of which are described at pages 347–405 of *The Image Processing Handbook* mentioned above. Example object definition protocols provided in one embodiment of the invention are described in more detail with reference to FIG. 7.

Next, at block 18, each defined object is separately numerically characterized by a set of parameters which are calculated from the pixel locations and brightness values of each defined object. In general, the numerical parameters are measures of the object's shape, size, brightness, color, and other calculated characteristics. Preferably, the values present in the parameter sets are similar for objects of the same type. Example parameters which may advantageously be used in embodiments of the invention are described below with reference to FIG. 3.

Referring now to block 20, a template for comparison is defined by the user. The template may be a single defined object, or may be a group or cluster of defined objects in a region of the image. At block 22, similarities between the template and other objects or sets of objects are calculated. If the template is a single object, this may be done by comparing the parameter set assigned to the template object with the parameter sets assigned to other objects. There are several well known ways of evaluating the similarity between two parameter vectors. For example, Euclidean or Minkowski line metrics may be used. If the parameter set is represented as a bit string, the Hamming distance may be used as the similarity measure.

In certain embodiments of the invention, multi-dimensional non-binary parameter sets are associated with the objects, and as stated above, a comparison may be performed between not only individual parameter sets but also between parameter set groups associated with clusters of a plurality of objects. In this case, a more complicated formula has been developed and may be used, based on ideas set forth in Voronin, Yu. A., *Theory of Classification and Its Applications* 1985, published in Russia by Nauka. This formula is set forth fully below. As is also explained below, if the template comprises a set of two or more objects, the comparison involves not only a comparison of the objects themselves, but also the spatial relationship between them.

It will be appreciated that accuracy in identifying similar objects is improved when the filtering and object definition steps described above result in the enhancement of object features which are associated with objects of the desired class but not associated with objects not in the desired class. These enhanced features will manifest themselves as a numerically discriminable part of the parameter set, and the parameter set may thus be utilized to differentiate objects in the desired class from objects outside the desired class.

As one specific example, a query image may comprise a digital image of an area of skin pigmentation. A physician may be interested in evaluating the likelihood that the pigmentation in the image is a melanoma. Using a method according to the present invention, the digital image is filtered and an image area associated with the pigmentation is defined as an object within the image. Other images of skin pigmentation which are stored in an image database are also filtered and areas of skin pigmentation are defined as objects, advantageously using the same filters and object definition functions. These objects in the database are then also parameterized. The query parameter set is compared to the parameter sets associated with the database objects, and images of skin pigmentation which are similar are identified. Advantageously, the pigmentation area of the stored images have been previously characterized as being melanoma or not. If retrieved similar object images are predominantly images of melanomas, the physician may be alerted that the possibility of melanoma for the query image is high. As mentioned above, it is advantageous if the filtering and object definition procedures enhance those aspects of skin pigmentation images which are closely associated with the presence of a melanoma. Furthermore, the parameter set itself may be tailored to the class of objects being analyzed. This may be done by assigning different weights to the different parameters of the parameter set during the comparison. For the melanoma example, a high weight may be assigned to parameters which are indicative of an irregular boundary or surface, while a lower weight may be assigned to a parameter associated with the total area of the object.

Figure 2:
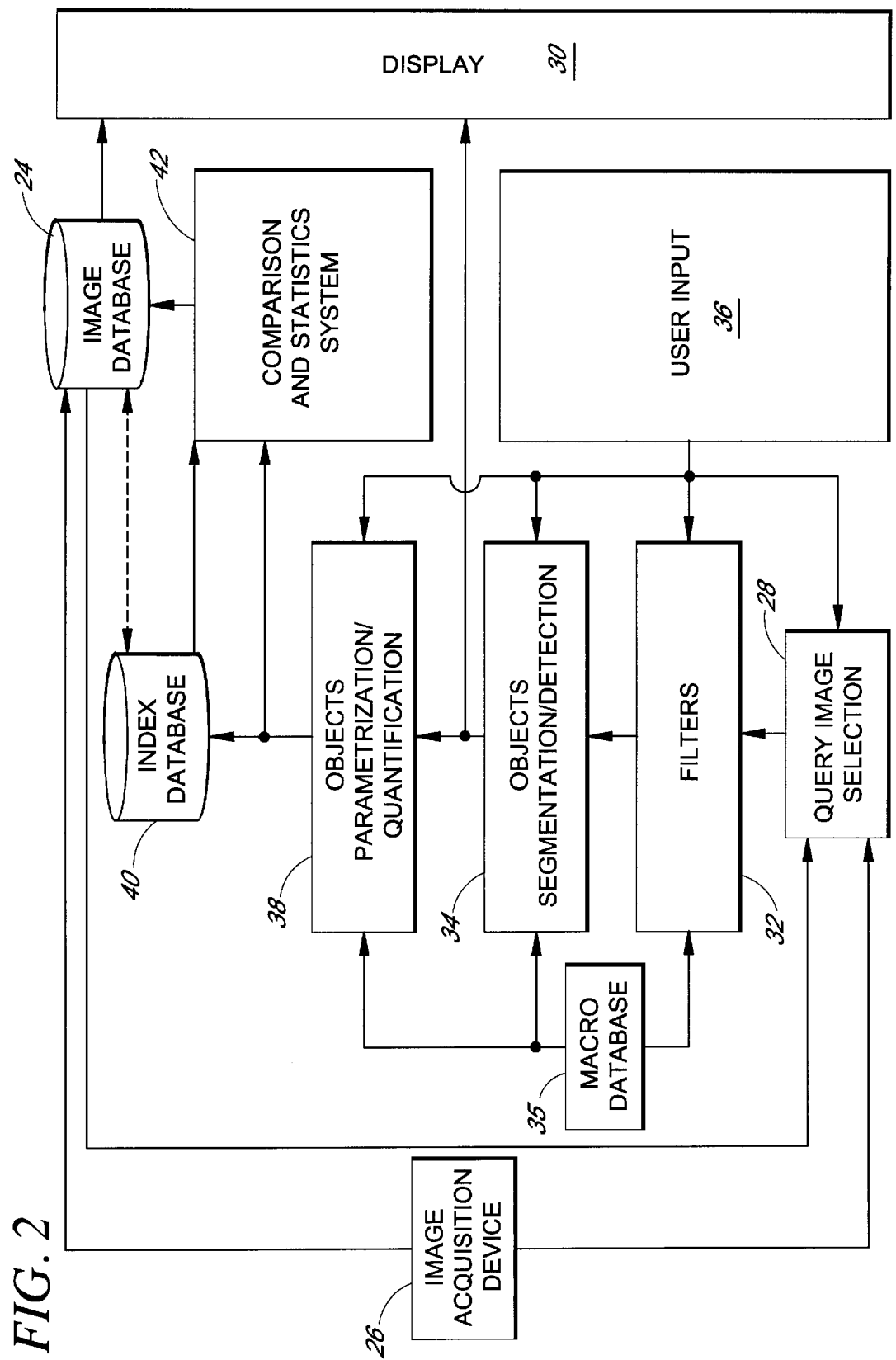
FIG. 2 is a block diagram of an image retrieval system according to the invention which may be utilized to carry out the method of FIG. 1.

A system which may be used in one embodiment of the invention is illustrated in FIG. 2. An image acquisition device 26 is used to initially create images for storage in an image database 24 and/or for routing to a query image selection module 28 of the system. The image acquisition device may be a source of images of any type, including photographs, ultrasound images, X-ray or MRI images, a CRT display or trace, or any other data source having an output, which is definable as a collection of digital values. The image acquisition device may, for example, be a digital camera. The image acquisition device may produce the image directly. The system may also import previously created images from one or more image sources. The image acquisition device may be an external digital image source for such systems like the Internet or Telnet, for example. Typically, of course, the image data array processed by the system will be a two-dimensional array of pixels wherein each pixel is assigned an associated scalar or vector value. For grey scale images, each pixel is associated with a brightness value, typically eight bits, defining a gray scale from zero (black) to 255 (white). For color images, a three component vector of data values may be associated with each pixel. The query image selection module, may, under the control of a user, select a query image from the image acquisition device, or may retrieve an image from the image database 24.

The system also comprises a display 30 which provides a visual output of one or more images to the user of the system. For example, the query image itself will typically be displayed to the user with the display device 30. This display of the query image may further be performed after image filtering by the filter module 32 and object definition by the object definition module 34. If no filtering or object segmentation has yet been implemented by the user with these modules, the unprocessed query image will be displayed to the user.

With a user input device 36 such as a keyboard, touchpad, or mouse, the user may control the filter module 32 so as to implement the filtering described above with reference to block 14 of FIG. 1. It is one aspect of some embodiments of the invention that the image continues to be displayed as the filtering is implemented. Thus, as the user modifies the filter function being performed by the filter module 32, the visual impact of the filter application on the image is displayed to the user.

The user may also control the implementation of object definition by the object definition module 34. Pixel brightness thresholds and other features of the object definition procedure may be modified by the user with the input device 36. As with the filtering operation, the image may be displayed after object definition so that the user can observe visually the contours and internal features of objects defined in the image. If the object definition technique is modified by the user, the display of the image may be accordingly updated so that the user can evaluate the effects of the alteration graphically on the display.

In some embodiments, the user may allow the system to perform object definition automatically, without requiring any additional user input. Of course, the above described display updates may be performed after this automatic object definition as well. As is also illustrated in this Figure and is explained further below with reference to FIG. 4, the user may also control aspects of parameter calculation via the user input device 36.

It will also be appreciated that in many applications, multiple images having similar sources and structures will be processed by the user in the same way. For example, cranial X-ray images may all be processed with the same filter set and object definition functions prior to parameterization. This helps ensure that compatible images and objects therein are parameterized for comparison. Of course, care must be taken that the sources of the images are themselves compatible. Overall brightness, dimensional variations, and other differences between, for example, different microscopes used to obtain the query image and images in the database 24 should be compensated for either prior to or as part of the processing procedures, known as dimension and/or brightness calibration.

To facilitate this common processing of multiple images user defined macros of filter and object definition and detection functions may be stored in a macro database 35 for future use on additional images. The user-friendliness of the system is improved by this feature because images from similar sources can be processed in the same way without requiring the user to remember and manually re-select the same set of filtering and object definition functions when processing similar images in the future. In one embodiment, the user may operate on an image using either individual filter and object definition functions stored in the macro database or user defined groups of individual filter and object definition functions stored in the macro database 35.

The object definition module 34 is connected to an object parameterization module 38, which receives the pixel values and contour coordinates of the objects defined in the image. This module then calculates the parameter sets described above with reference to block 18 of FIG. 1 using the input pixel values. The calculated parameter sets may be stored in an index database 40 for future use. During the image searching and retrieval process, one or more parameter sets associated with a template will be forwarded to a parameter set comparison module 42 along with parameter sets associated with other objects in the image or other objects in images stored in the image database 24. Objects or object clusters, that are similar to the template, are then also displayed to the user on the display 30.

Figure 3:
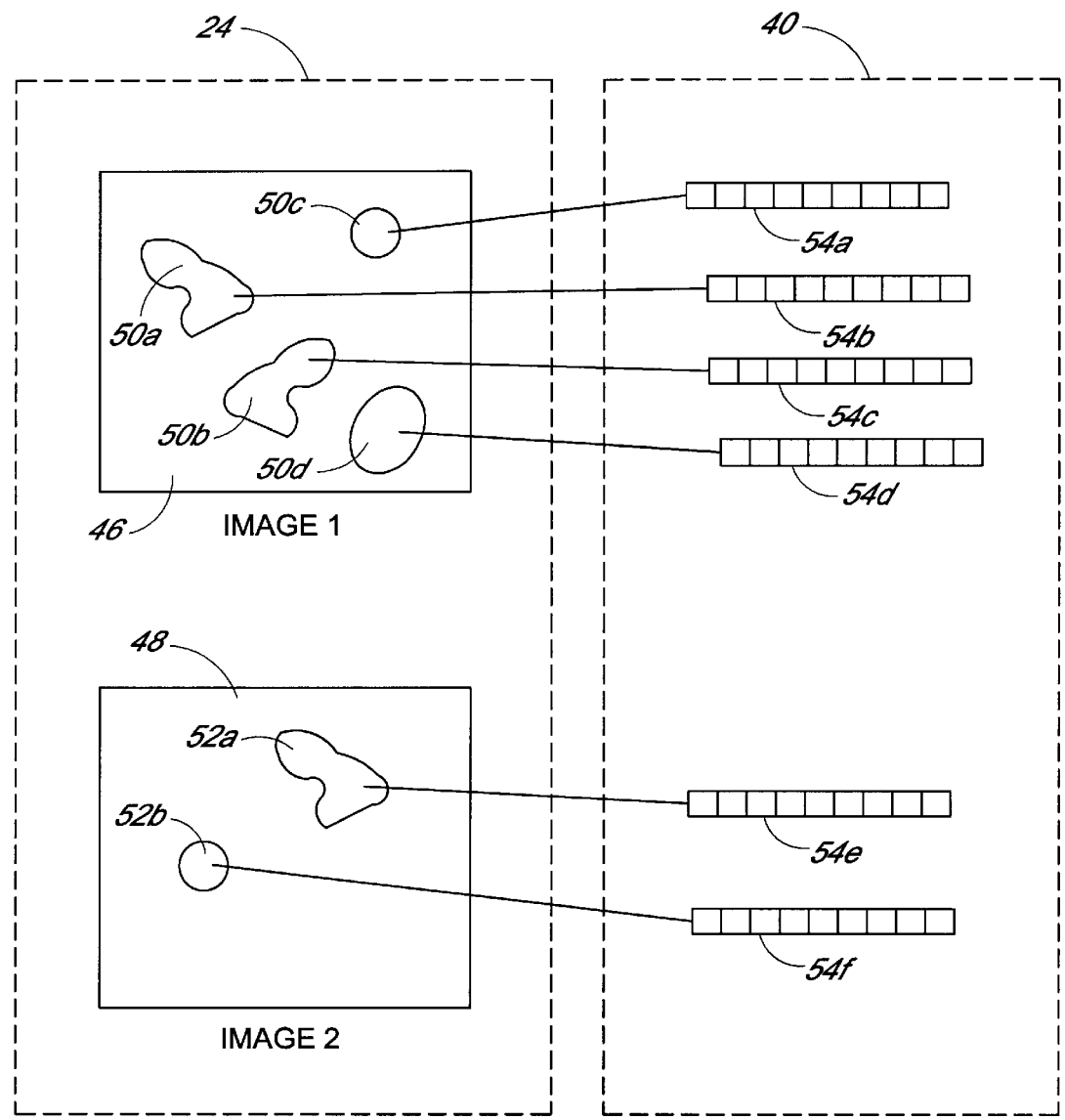
FIG. 3 is a conceptual schematic of parameter sets associated with objects segmented from an image which may be created by the object parameterzation module of FIG. 2.

Referring now to FIG. 3, it is one aspect of the invention that any given image may have associated with it several different parameter sets, with each parameter set associated with a detected object in that image. Thus, the image database 24 may store a plurality of images 46, 48, each of which includes a plurality of defined objects 50a–d and 52a–b. Each object is associated with a parameter set 54a–f, which is stored in the index database 40.

In one embodiment, the parameter set includes a computation of the object area by a formula which counts the number of pixels defined as part of object "A" and multiplies that number by a calibration coefficient as follows:

$$\sum_{i,j} z * \delta_{ij}, \delta_{ij} = \begin{cases} 1, & ij \in A \\ 0, & ij \notin A \end{cases}, \quad (1)$$

where z is a user defined dimensional calibration coefficient.

When the object has many internal holes, the area parameter may be calculated instead by the formula:

$$\frac{\sum_i (X_i + X_{i-1}) * (Y_i + Y_{i-1})}{2}, \quad (2)$$

wherein X, Y are the coordinates of the periphery pixels of the object.

Other advantageous object characterization parameters include the length of the perimeter, and the maximum and minimum diameters of the object through the center of gravity of the object. These may be calculated with the formulas:

$$\sum_i \sqrt{(X_i - X_{i-1})^2 + (Y_i - Y_{i-1})^2} \quad (3)$$

for perimeter, $$4 * \sqrt{\frac{\overline{x^2} - (\overline{x})^2 + \overline{y^2} - (\overline{y})^2 + \sqrt{\left(\overline{x^2} - (\overline{x})^2 - \overline{y^2} + (\overline{y})^2\right)^2 + 4*(\overline{xy} - \overline{x}*\overline{y})^2}}{2}}, \quad (4)$$

for maximum diameter, and $$4 * \sqrt{\frac{\overline{x^2} - (\overline{x})^2 + \overline{y^2} - (\overline{y})^2 - \sqrt{\left(\overline{x^2} - (\overline{x})^2 - \overline{y^2} + (\overline{y})^2\right)^2 + 4*(\overline{xy} - \overline{x}*\overline{y})^2}}{2}}, \quad (5)$$

for minimum diameter, where $$\overline{x} = \left(\sum_{j,i \in A} X_{ij}\right) \bigg/ \left(\sum_{j,i \in A} \delta_{ij}\right), \overline{y} = \left(\sum_{j,i \in A} Y_{ij}\right) \bigg/ \left(\sum_{j,i \in A} \delta_{ij}\right),$$

-continued $$\overline{x^2} = \left(\sum_{j,i \in A} X_{ij}^2\right) \bigg/ \left(\sum_{j,i \in A} \delta_{ij}\right), \overline{y^2} = \left(\sum_{j,i \in A} Y_{ij}^2\right) \bigg/ \left(\sum_{j,i \in A} \delta_{ij}\right),$$

$$\overline{xy} = \left(\sum_{j,i \in A} X_{ij} * Y_{ij}\right) \bigg/ \left(\sum_{j,i \in A} \delta_{ij}\right)$$

Other shape and size related parameters may be defined and included in the parameter set, such as form factor:

$$\frac{4 * \pi * \text{Area}}{(\text{Perimeter})^2} \quad (6)$$

equivalent circular diameter:

$$\sqrt{\frac{4 * \text{Area}}{\pi}} \quad (7)$$

and aspect ratio, which represents the ratio of the maximum diameter and minimum diameters through the center of gravity. The maximum and minimum Ferret diameters of the object may also be included as part of the parameter set, namely:

$$\max X_{ij} - \min X_{ij}; \max Y_{ij} - \min Y_{ij}, \quad (8)$$

where i, j ∈ A

Parameters which relate to pixel intensities within the object are also advantageous to include in the object characterization parameter set. These may include optical density, which may be calculated as:

$$-\log_{10}\left(\frac{\sum_{ij \in A} I_{ij}}{\sum_{ij \in A} \delta_{ij}} \bigg/ I_{\max}\right) \quad (9)$$

and integrated density:

$$\sum_{i,j \in A} I_{ij} \quad (10)$$

where $I_{ij}$ is the brightness (i.e. 0–255) of pixel ij, and $I_{max}$ is the maximium pixel brightness in the area/image.

More complicated intensity functions which parameterize the texture of the object may be utilized as well. One such parameter is a relief parameter which may be calculated as:

$$\sum_{i,j\in A; N_{ij}\geq 2} rl_{ij} \Big/ \sum_{i,j\in A; N_{ij}\geq 2} \delta_{ij}, \qquad (11)$$

$rl_{ij} = r_{ij} * \Omega(Nij)$; where $\Omega(N_{ij})$ is a function of $N_{ij}$ $$r_{ij} = \left(\sum_{m=i-1}^{i+1}\sum_{n=j-1}^{j+1} \text{abs}(I_{nm} - I_{ij})\right) \Big/ N_{ij}; n, m \in A;$$

$$N_{ij} = \sum_{n=i-1}^{i+1}\sum_{m=j-1}^{j+1} \delta_{nm}$$

This parameter belongs to a textural class of parameters and is a measure of the average difference between a pixel values in the object and the values of its surrounding pixels. In the simplest case, $\Omega(N_{ij})=N_{ij}$, although the function may comprise multiplication by a constant, or may involve a more complicated function of the number of nearest neighbors or pixel position within the object.

Other examples include homogeneity:

$$\Phi = \sum_{Ii}\sum_{Ij} (N_{ij}/\overline{N}(DiameterFerret_{xy}))^2, \qquad (12)$$

where I is intensity; i, j∈ A; and $\overline{N}$ is a renormaliz ing constant and contrast:

$$L = \sum_{Ii-Ij=0} (I_i - I_j)^2 \left[\sum_{Ii-Ij} (N_{ij}/\overline{N}(DiameterFerret_{xy}))\right], \qquad (13)$$

where I is intensity; i, j∈ A; and $\overline{N}$ is a renormaliz ing constant

It will be appreciated that the nature of the parameter set may vary widely for different embodiments of the invention, and may include alternative or additional parameters not described above. The parameters set forth above, however, have been found suitable for object characterization in many useful applications.

Figure 4:
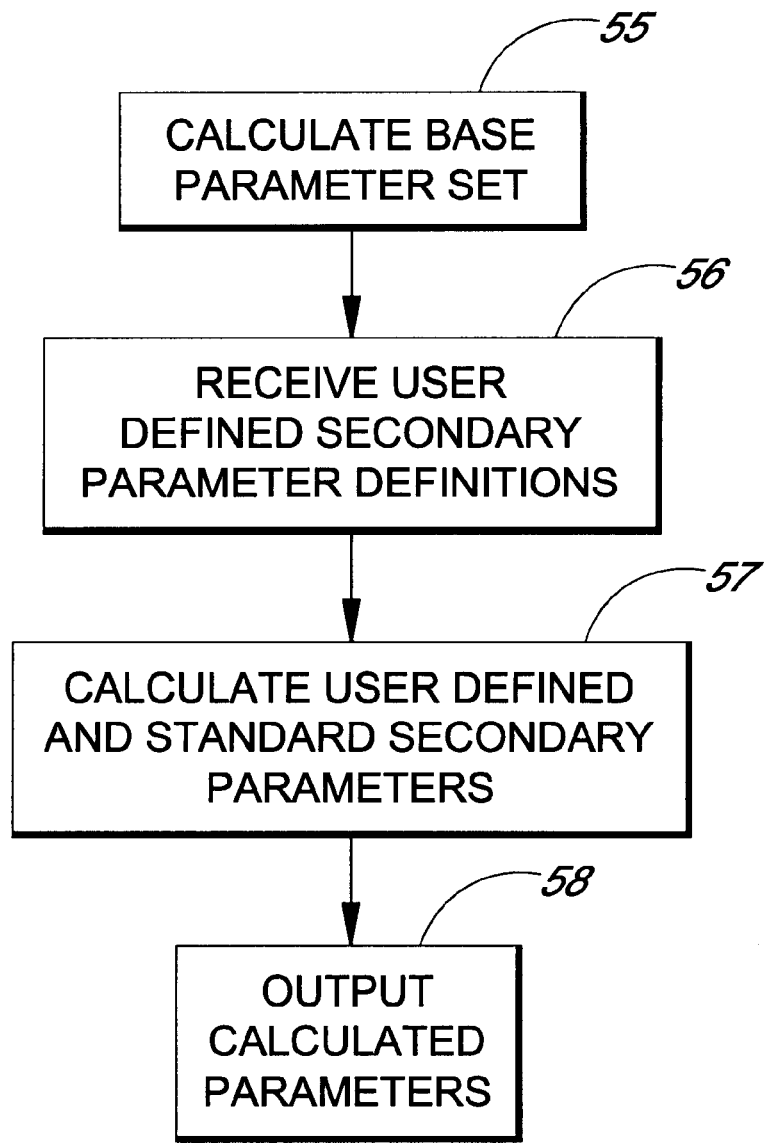
FIG. 4 is a flowchart of one embodiment of an object parameterization process which may be implemented in the object parameterization module of FIG. 2.

FIG. 4 illustrates a flowchart of the parameter set generation process which may be performed by the object paramterization module 38 of FIG. 2. Initially, at block 55, the base or fundamental parameters are calculated. These are the parameters that use raw pixel positions or intensities as inputs. Examples include area (Equation 1), perimeter (Equation 3), integrated intensity (Equation 10), etc. Another set of parameters, referred to herein as "secondary" parameters are also calculated. These are parameters which are functions of the base parameters, and which do not require any additional pixel specific information for their calculation. Examples of standard secondary parameters include formfactor (Equation 6) and aspect ratio. In some embodiments, the user is allowed to define additional secondary parameters for object characterization which may have significance in certain image analysis applications. For example, a new hypothetical parameter comprising the ratio of formfactor to area may be defined and made part of the object characterization parameter set. Thus, at block 56, the system may receive user input (by entering information into a dialog box with a mouse and/or keyboard, for example) regarding secondary parameter definitions not already utilized by the system.

At block 57 the system calculates both the user defined and standard secondary parameters, and at block 58 the parameters thus calculated are formatted into a feature vector and output to either or both the index database 40 and the comparison and statistics system 42 of FIG. 2.

In FIGS. 5 through 9, a specific implementation of the invention is illustrated by example screen displays which illustrate aspects of user control (via the input devices 36 of FIG. 2) and visualization (via the display 30 of FIG. 2) of the filtering and object definition processes. As will be apparent to those of skill in the art, this embodiment of the invention is implemented in software on a general purpose computer. A wide variety of data processing system environments may be utilized in conjunction with the present invention. In many embodiments, the invention is implemented in software coded in C/C++ programming languages and running on a Pentium series personal computer with, for example, 32 Mbytes of RAM and a 640 MB hard drive. The personal computer in this implementation will typically be connected to an image database through a local or wide area network, or via Internet/Telnet client-server system. In another implementation, the personal computer runs a standard web browser, which display a communicating application and accesses image databases and image analysis and computer-aided detection software hosted on a remote Internet server. Intranet version of the application is also envisioned and implemented. In such case the system works as a part of PACS, for example, using LAN and HIS as a hosting system.

Figure 5:
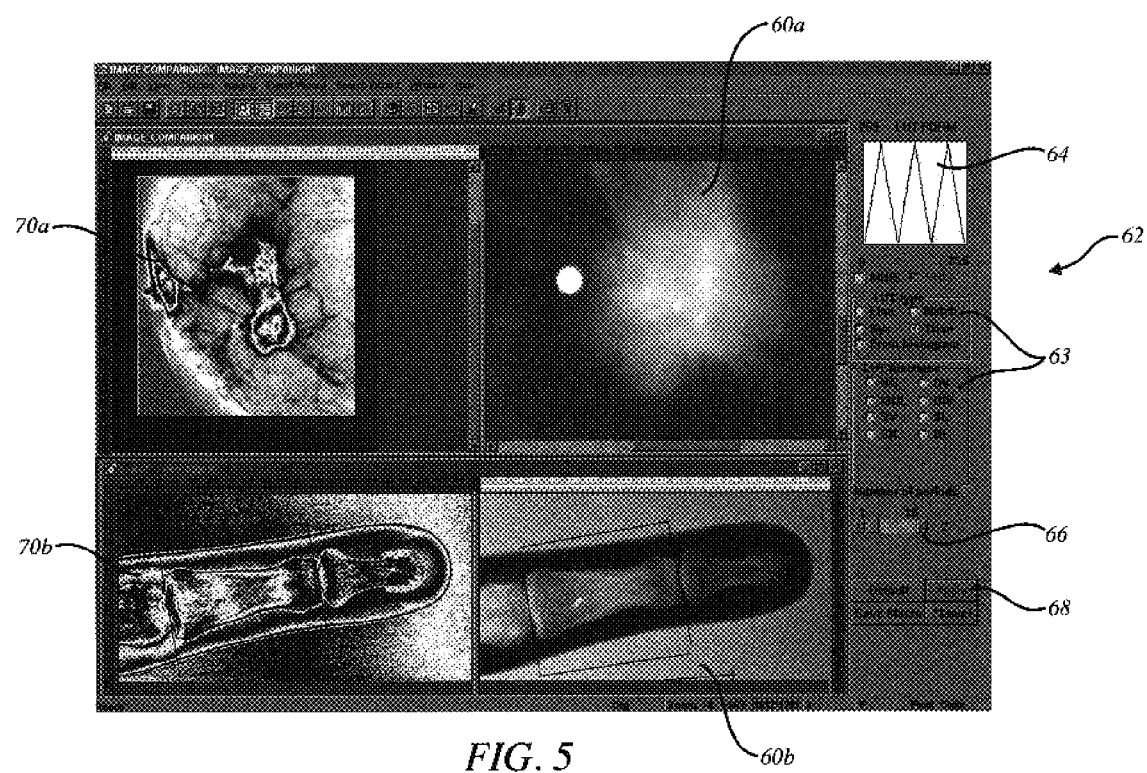
FIG. 5 is a screen display of user configured look up table filter functions according to one embodiment of the invention and which may be generated by the system of FIG. 2.

Referring now to FIG. 5, original images 60a and 60b are displayed to the user of the system in respective portions of the display. The upper display 60a comprises a close up of a suspected malignancy in a mammogram. The lower display 60b is a bone density image utilized in evaluating osteoporosis. On another portion 62 of the screen is a display of a filter protocol. This portion 62 of the screen display shown one of the computationally simplest filtering techniques under user control in this embodiment, which is look-up-table (LUT) filtering. With this filter, each input pixel brightness value is mapped onto an output pixel brightness value. If pixel brightness ranges from a value of 0 (black) to 255 (white), each value from 0 to 255 is mapped to a new value defined by the LUT being used.

In this embodiment, the user is provided with a visual indication 64 of the look-up table form being applied, with input pixel values on the horizontal axis and output pixel values on the vertical axis. Using user selectable check boxes 63, the user may define the nature of the look-up-table filter being applied. In this embodiment, the user may define both a table form and a table function. The form may be selected between linear (no effect on pixel values), triangular, and sawtooth (also referred to as notch). The triangular form is illustrated in FIG. 5. For the triangular and sawtooth forms, the user may be provided with a slidebar 66 or other input method for selecting the number of periods in the input brightness range. The user may also import a previously used user defined LUT if desired.

The look-up-table form may also be varied by additional user defined functions. These functions may include negative inversion, multiplication or division by a constant, binarization, brightness shifting, contrast stretching, and the like. For each of these functions, the user may control via slidebars or other user manipulatable displays the constants and thresholds utilized by the system for these functions. Histogram based look-up table filtering may also be provided, such as histogram equalization and histogram based piecewise contrast stretching. After the user defines the desired LUT filter, they may apply it to the image by selecting the "APPLY" button 68. The look-up-table defined by the user is then applied to the image or a selected portion thereof.

Furthermore, second display 70a and 70b of the image is provided following application of the three period triangular LUT filter. If the user modifies the LUT filter function, the image display 70a, 70b is updated to show the visual result of the new filter function when the user clicks the APPLY button 68. Thus, the user may view a substantially continuously updated filtered image as the filter functions used are modified. In filtered image 70a, regions of suspected malignancy are enhanced with respect to the background following LUT application. In the filtered image 70b, the bone density variations present in the central bone segment are enhanced and pronounced.

Figure 6:
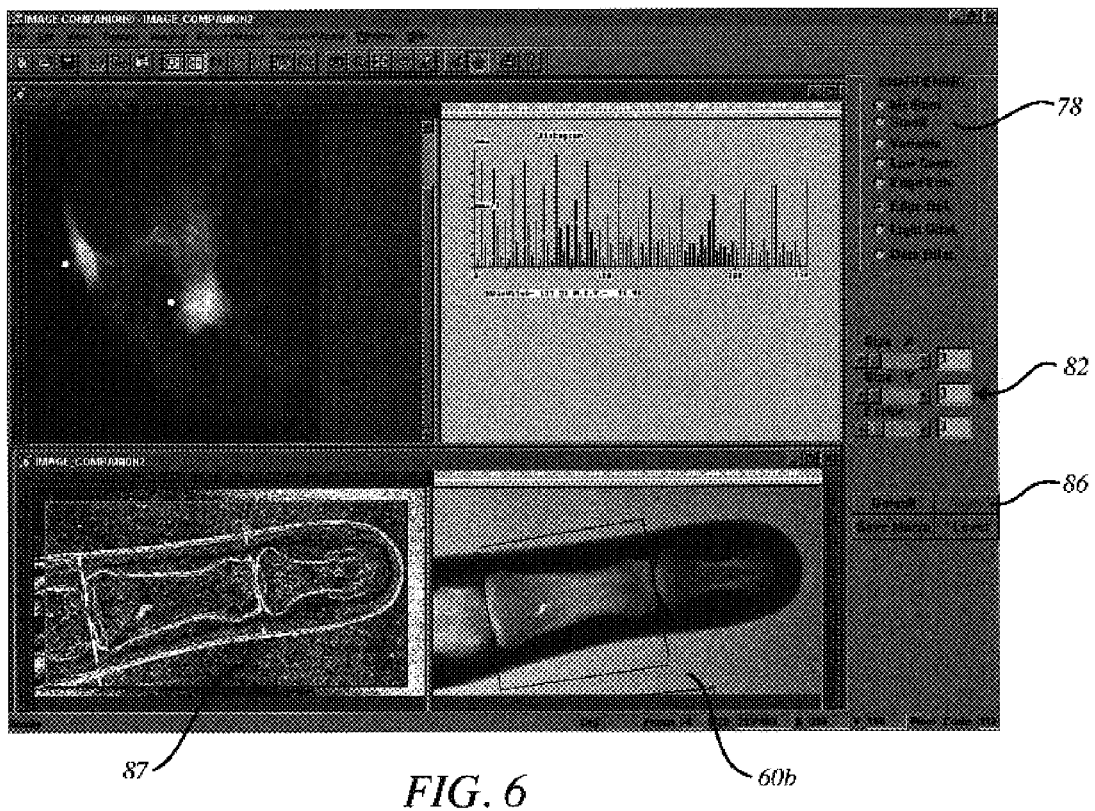
FIG. 6 is a screen display of user configured sharpening filter functions according to one embodiment of the invention and which may be generated by the system of FIG. 2.
Figure 7:
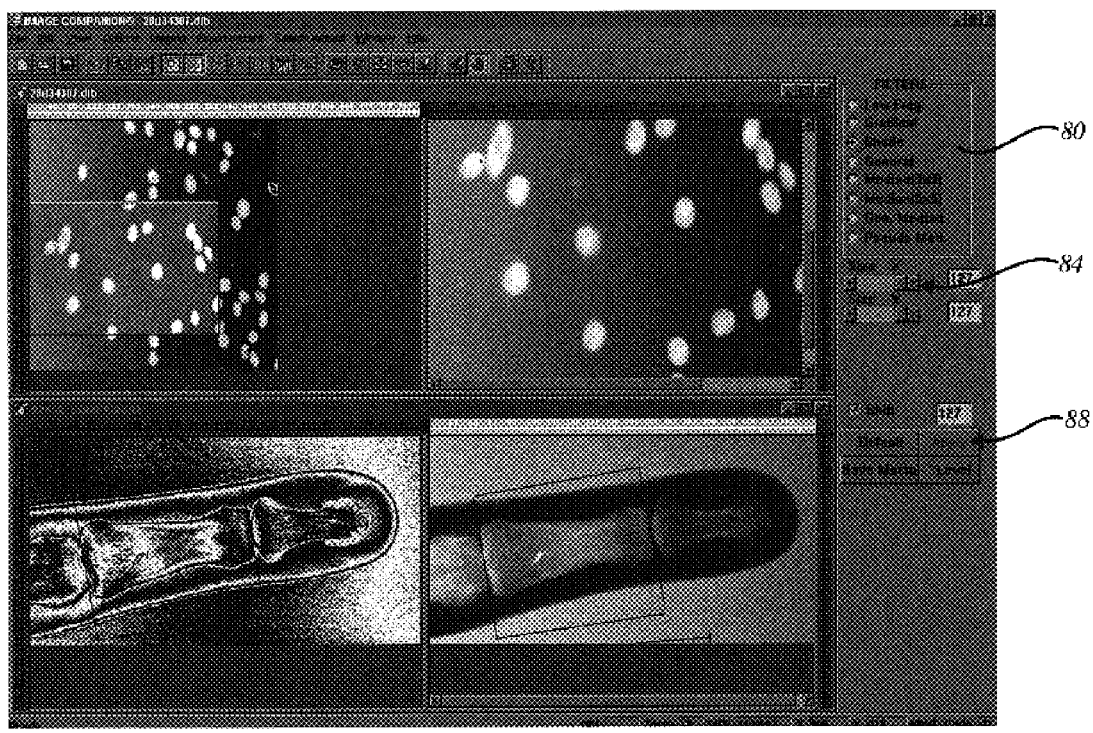
FIG. 7 is a screen display of user configured general and edge enhancement filter functions according to one embodiment of the invention and which may be generated by the system of FIG. 2.

In addition to LUT filtering, convolution filters, frequency domain filters, and other filter types may be utilized to further enhance and define significant features of imaged objects. Several specific examples provided in one embodiment of the invention are illustrated in FIGS. 6 and 7. In analogy with the user interface for the LUT filtering described with reference to FIG. 5, additional filter types may be selected with checkboxes 78, 80. Filter parameters such as filter box size are user controllable via slidebars 82, 84. APPLY buttons 86, 88 initiate the filter operation and display update to show the filtered image or image region. In FIG. 6, the bone image 60b is filtered with a 3×3 edge detection filter which produces the filtered image 87 having enhanced pixels along edges in the image. In FIG. 7, a region of interest 89 in an image of blood cells in bodily fluids where a shading filter was used to compensate for a background brightness variation across the image.

In the specific implementation illustrated in FIGS. 6 and 7, the following base set filter functions may be applied by the system user:

1. Sharpening of Small Size Details on Image

This type of filter belongs to a class of Laplacian filters. The filter is a linear filter in the frequency domain. The 3×3 kernel is understood to mean that central pixel brightness value is multiplied by 4. As a result of this filtering, the sharpness of small details (not to exceed 3×3) of the image is increased.

$$C_{mn} = \begin{Bmatrix} -1 & -1 & -1 \\ -1 & 9 & -1 \\ -1 & -1 & -1 \end{Bmatrix}$$

2. Sharpening of Middle Size Details on Image

This type of filter belongs to a class of Laplacian filters. Functionality is similar to the 3×3 kernel type filter. As a result of this filtering, the sharpness of small details (not to exceed 5×5) of the image is increased.

$$C_{mn} = \begin{Bmatrix} -1/12 & -1/12 & -2/12 & -1/12 & -1/12 \\ -1/12 & -2/12 & 3/12 & -2/12 & -1/12 \\ -2/12 & 3/12 & 28/12 & 3/12 & -2/12 \\ -1/12 & -2/12 & 3/12 & -2/12 & -1/12 \\ -1/12 & -1/12 & -2/12 & -1/12 & -1/12 \end{Bmatrix}$$

3. Sharpening of a Defined Size Details on Image

This filter performs convolution transformation of the image through a user defined multiplication factor. As a result, all details of a user defined size are sharpened. The size of processed image detail may be defined through available editing submenu windows for X and Y dimensions.

$$I_{out} = I_{in} * \vartheta * \left(I_{in} - \sum_{\Omega} I_{in}/(m*n)\right), \text{ where } \vartheta \text{ is the user} \quad (14)$$

defined multiplication factor and $\Omega$ is the $m \times n$ filter box

4. Sharpening of a Low Contrast Details

This filter performs convolution transformation of the image and belongs to a spatial domain filters. The filtering is performed through a user defined multiplication Factor and automatically calculated special parameter. This parameter is a ratio of a current pixel value to Mean Square Deviation of a pixel value calculated for the given size of the pixel aperture (or filter box). As a result, all details of a user defined size are sharpened. The size of the processed image detail may be defined through available for editing submenu windows for X and Y dimensions.

$$I_{out} = I_{in} * \vartheta * \mu * \left(I_{in} - \sum_{\Omega} I_{in}/(m*n)\right), \quad (15)$$

where $\vartheta$ is factor and $\mu$ is $\left(\sum_{\Omega} I_{in}/(m*n)\right)\Big/\sigma_{\Omega}$ 5. Edge Enhancement Filter This edge enhancement filter belongs to a non-linear range filter. User defines the size of the filter box. This filter provides two regimes, selected by the user. If the default regime Strong is changed by the user to regime Weak, the filter will change the processing method to avoid images noise impact in certain high frequencies.

$I_{out}=\text{Sup}_\Omega$, when $I_{in}>\frac{1}{2}*(Sup_\Omega+Inf_\Omega)$ $I_{out}=\text{Inf}_\Omega$, when $I_{in}>\frac{1}{2}*(Sup_\Omega+Inf_\Omega)$ (16)

where $\text{Sup}_\Omega$ is maximum brightnesss within filter box and $\text{Inf}_\Omega$ is minimum brightness within filter box 6. Edge Detection This edge detection filter belongs to modified Laplacian omnidirectional edge detection convolution filters. User defines the size of the filter box. This filter performs edge detection of the image through a user defined Factor. The Factor is used for convolution mask values calculations 7. Dilation Filters Both filters belong to morphological class and are inversive to each other. The first one should be used for image light elements dilation, the second one—for dark elements dilation. If the default regime Strong is changed by the user to regime Weak, both filters will change the processing method to avoid images noise impact in certain high frequencies. In general:

$I_{out}=\text{Sup}_\Omega$ or $I_{out}=\text{Inf}_\Omega$ (17)

8. Low Frequency

This filter represents a convolution transformation of modified Gaussian type. It belongs to a class of linear filters in frequency domain. The size of pixel box or aperture is defined by the user for X and Y dimensions. The filter is used often for certain frequencies noise reduction. In general:

$$I_{out} = \left(\sum_{\Omega} I_{in}/(m*n)\right) \quad (18)$$

9. Gradient/Modified Sobel Edge Detection Filter

This filter belongs to a non-linear edge-detection class. The filter uses a technique with partial derivatives replacement with their estimates. It is known in image processing as a Sobel filter. The size of the pixel box or aperture defined by the user for X and Y dimensions. This filter performs convolution transformation of the image through a user defined amplification Factor. The user also is provided with the ability to set a binarization Threshold if a correspondent check-box is marked. The threshold serves as a modification to the classic Sobel filter and enables the user to find right flexibility for the edge detection process. If the threshold is used the outcome of transformation will be a binary image. The default but modifiable masks are:

$$C_{mn} = \begin{Bmatrix} 1 & 0 & -1 \\ 2 & 0 & -2 \\ 1 & 0 & -1 \end{Bmatrix} \quad C_{mn} = \begin{Bmatrix} -1 & -2 & -1 \\ 0 & 0 & 0 \\ 1 & 2 & 1 \end{Bmatrix}$$

10. Shading Correction

This filter belongs to a smoothing class filter. The size of the pixel box or aperture is defined by the user for X and Y dimensions. The filter is modified from a classical type shading correction filter by enabling the user with shifting capability. If check-box Shift is marked the user will be able to change the default value of the shift to a custom one. This filter is very handy for elimination of a negative lighting impact which sometimes occurs during the image acquisition process.

$$I_{out} = \left( I_{in} - \sum_{\Omega} I_{in}/(m*n) \right) + \text{Shift,} \quad \text{where Shift dy default is 127} \tag{19}$$

11. General or Universal Filter

This is a convolution type filter with a user controlled size of the kernel and the weights mask values. The default size of the kernel is 9×9. For the user's convenience, the convolution mask contains default typically used weights values. Push-button activates the customization regime when the user is able to modify dimensions of the mask and then modify default weights in the convolution mask.

12. Median (3×3) filter

Moving median (or sometimes referred as rank) filter produces as an output the median, replacing a pixel (rather than the mean), of the pixel values in a square pixel box centered around that pixel. The filter is a non-linear type filter with the filtration window dimensions of 3×3. Usually used to eliminate very small details of the image sized at 1–2 pixels.

13. Median (5×5) filter

Similar to the filter described above, but with the filtration window dimensions 5×5. Usually used to eliminate small details of the image sized at up to 5 pixels.

14. General Median Filter

This filter is similar to the filters described above, but with the filtration window dimensions set by the user. The size of eliminated details depend on the size of the set filtration window.

15. Psuedomedian Filter

Figure 8:
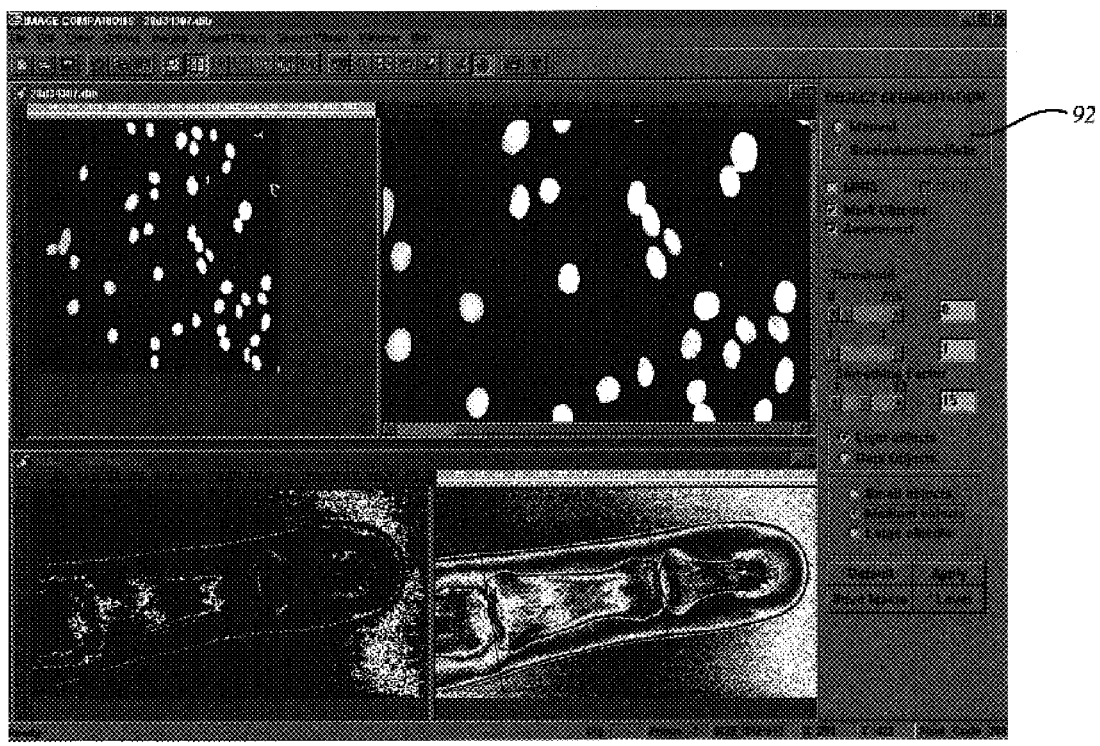
FIG. 8 is a screen display of user configured object definition according to one embodiment of the invention and which may be generated by the system of FIG. 2.

This filter is similar to median type filters described above. However it provides rectangular filtration window controlled by the user and performs transformation in a two pass algorithm User control of object definition (corresponding to module 34 of FIG. 2) is illustrated in FIG. 8. By selecting one of the checkboxes 92, the user implements manual or semi-automatic object definition. In manual mode, slidebars allow the user to select a brightness range of pixels. All pixels outside this range are considered background. An object is thus defined as a connected set of pixels having brightness values in the user defined range. Background pixels may be reassigned a zero brightness value. In the automatic mode, the user interface for which is illustrated in FIG. 8, the thresholds are calculated automatically by the system from the image histogram. In this mode, the system may allow the user to set up multiple thresholds by setting their values manually or by choosing their sequential numbers from the automatically calculated table of thresholds.

As was the case with the filtering process, the image (or region of interest) is displayed as the object definition function is applied. Those of skill in the art will understand that a wide variety of techniques for assigning pixels to objects or background are known and used, any one of which now known or developed in the future may be used in conjunction with the present invention.

Figure 9:
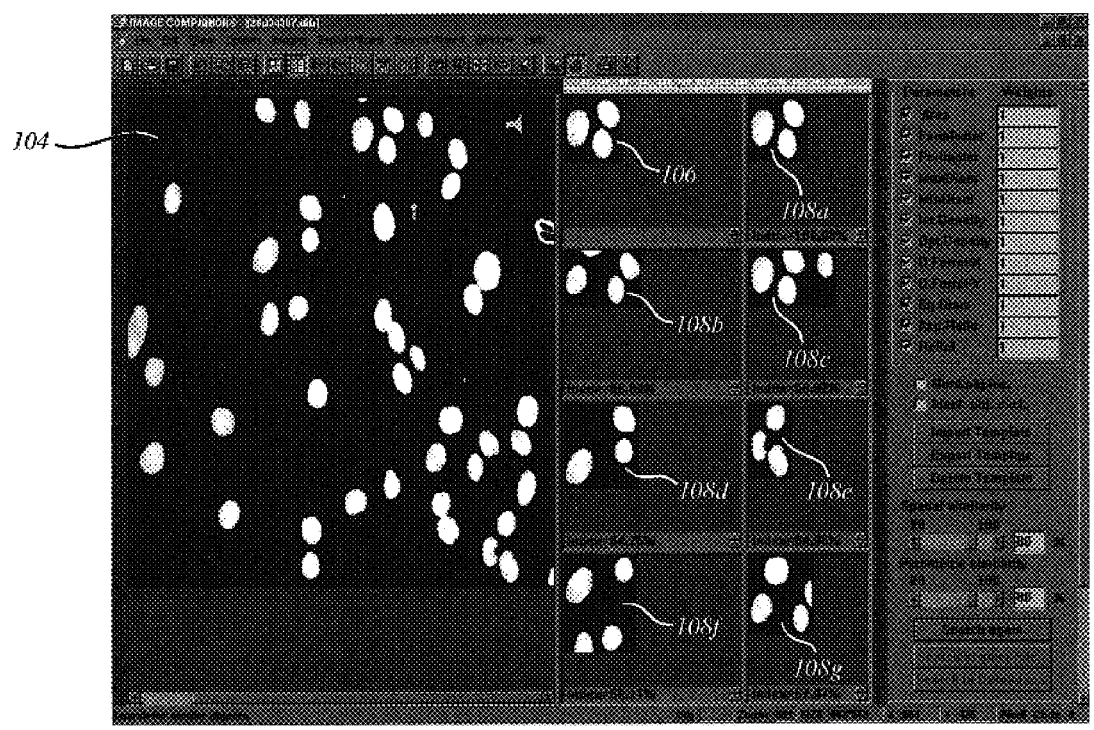
FIG. 9 is a screen display of user configured object searching and comparison according to one embodiment of the invention and which may be generated by the system of FIG. 2.

After objects are defined/detected, parameter sets are calculated for each object, and then comparisons are possible to find similar objects (or object clusters as discussed above) in either the same image or in different images. This is illustrated in FIG. 9, which shows a display of the original image 104 after filtering and object segmentation, as well as the template 106 selected for comparison to objects in the remainder of the image. In this example, the template 106 is a three object cluster. Also provided in this screen display are seven displays 108a–g which display in rank order the seven objects of the image most similar to the template object. Also displayed at 110 is a list of the parameters used in the comparison and the weights assigned to them for the comparison process. These weights may be manually set, or they may be set via a statistical process which is described in further detail below.

The actual comparison process which defines the degree of template similarity may, for example, be performed with the following formulas. For templates consisting of one individual parameterized object, a parameter difference vector may be computed which has as each element the difference between the parameter values divided by the maximum difference observed between the template object and all objects being compared to the template.

$$\Delta_{it}(P_{it}, P_j)/\Delta\max(P_{it}, P_k), \tag{20}$$

where

P is a parameter-vector; $_{it}$ is the index of template object; $_k$=1, . . . ,L; L is all objects that the template object is being compared to; and $_j$ is the index of specific object being compared to template object.

A numerical similarity may then be computed using either a modified form of Euclidean or Minkowski line metrics as set forth below:

$$\begin{cases} \left( \sum_{k=1}^{L} (p_k^t - P_k^t)^s * \omega_k \right)^{1/s} \text{ and} \\ (P_i - P_k)^T W^{-1}(P_i - P_k), \\ \text{where } W \text{ is the covariation matrix;} \\ \omega \text{ is a statistical weight} \end{cases} \tag{21}$$

$$p = p_k^t/(\max p_k - \min p_k)$$

For multi-object templates or entire images, the spatial relationship between selected objects of the template to other objects in the template may be numerically characterized and effectively added as one or more additional sub-vectors of the object parameter vector. The overall similarity between a multi-object template and object clusters in the image database, may, in some embodiments of the invention be calculated as follows:

$$\zeta = \sum_{j=1}^{Z} \varpi * \text{abs}(\eta_{ij}^t)/Z, \tag{22}$$

$$\eta_{ij}^t = 1 - \text{abs}(\Delta_i^t - \Delta_j^t)/(\max\Delta_t - \min\Delta_t),$$

-continued $$\Delta^t = \begin{cases} 1, & \text{when abs}(\Delta_i^t - \Delta_j^t) \le \varepsilon_t \\ 0, & \text{else} \end{cases}$$

$\epsilon$ is a thresholds and/or tolerances vector, $\omega$ is a weights vector This formula combines not only parametric similarity but spatial similarity also. For spatial similarity the closeness of the position and pattern fit for objects of the template and objects of the database are numerically evaluated. The mathematical method for parameterizing these spatial relationships may, for example, use some simple Euclidean distances between objects for primitive cases and up to pattern fit calculations based on second, third, or fourth moments of inertia for comparable components in complex cases.

Once the objects are parameterized and the template is defined as either a single object or a cluster of objects, the comparison calculation involves the mathematical generation of a value which characterizes how "similar" two vectors or matrices of numbers without further reference to the meaning associated with those numbers. A wide variety of mathematical techniques are available to perform such a numerical characterization, and different approaches may be more suitable than others in different contexts. Thus, the specific formalism used to mathematically define and quantify similarity between number sets may vary widely in different embodiments of the invention and different techniques may be appropriate depending on the application.

As discussed above, the weight assigned to a given parameter during this comparison process may be manually set by the user or set using a statistical method. The statistical method is especially useful when the database of images includes a large number of objects which have been characterized as having or not having a characteristic trait, such as an area of skin pigmentation is either melanoma or not melanoma, or which have been characterized numerically as more similar or less similar to a "model" object. When this data is available, it can be analyzed to determine how strongly different parameters of the parameter set values correlate with the presence or absence of the specific trait.

The weight used for a given parameter in the comparison process may thus be derived from the values of the parameter vectors associated with the detected objects in the image database.

In using this method a system is represented as a totality of factors. The mathematical simulation tools are correlation, regression, and multifactor analyses, where the coefficients of pairwise and multiple correlation are computed and a linear or non-linear regression is obtained. The data for a specific model experiment are represented as a matrix whose columns stand for factors describing the system and the rows for the experiments (values of these factors).

The factor Y, for which the regression is obtained, is referred to as the system response. (Responses are integral indicators but theoretically, any factor can be a response. All the factors describing the system can be successively analyzed.). The coefficients of the regression equation and the covariances help to "redistribute" the multiple determination coefficient among the factors; in other words the "impact" of every factor to response variations is determined. The specific impact indicator of the factor is the fraction to which a response depending on a totality of factors in the model changes due to this factor. This specific impact indicator may then be used as the appropriate weight to assign to that factor (i.e. parameter of the parameter set associated with the objects).

The impact of a specific factor is described by a specific impact indicator which is computed by the following algorithm:

$$\gamma_j = \alpha * [b_j * c_{0j}], j=1,2,\ldots k, \quad (23)$$

where $\gamma$ is the specific impact indicator of the j-th factor; k is the number of factors studied simultaneously; $b_j$ is the j-th multiple regression coefficient which is computed by the formula $$X_0 = a + \Sigma b_j * X_j, \quad (24)$$

where $X_0$ is the system response to be investigated, a is a free term of the regression, and $X_j$ is the value of the j-th factor. The coefficient $\alpha$ of the equation is computed by the formula $$\alpha = R^2 / [\Sigma_j | b_j * c_{0j} |], \quad (25)$$

where R is the coefficient of multiple determination computed by the formula $$R = [(n^2 * \Sigma_j b_j * c_{0j}) / (n * \Sigma_j x^2_{0j} - (\Sigma_j x_{0i})^2)]^{1/2}, \quad (26)$$

where n is the number of observations, which cannot be below $(2*K)$; $x_{0i}$ is the value of the system response in the i-th observation, $c_{0j}$ is the covariance coefficient of the system response indicator and the j-th factor. It is given by the relation $$c_{0j} = (n * \Sigma_i x_{0i} * x_{ji} - \Sigma_i x_{0i} * \Sigma_i x_{ji}) / n^2 \quad (27)$$

The specific contribution indicator is obtained mainly from the coefficient of multiple determination, which is computed by the formula $$R^2 = (\Sigma_j b_j * c_{0j}) / D^2 \quad (28)$$

where $D^2$ is the response variance. The specific impact of the j-th factor on the determination coefficient depends only on the ratio of addends in this formula. This implies that the addend whose magnitude is the largest is associated with the largest specific impact. Since the regression coefficients may have different signs, their magnitudes have to be taken in the totals. For this reason, the coefficients $\gamma$ of the specific impact are bound to be positive. However, it is important that the direction in which the factor acts by the computed $\gamma$ is dictated by the sign of the regression coefficient. If this sign is positive, the impact on the response variable is positive and if it is not, the increase of the factor results in a reduction of the response function. The influence of the background factors, which are not represented in the data, is computed by the formula $$\bar{\gamma}_j = 1 - \Sigma_j \gamma_j. \quad (29)$$

The importance of the $\gamma$ is determined from the relation for the empirical value of the Fisher criterion $$F_j = (\gamma_j * (n-k-1)) / (1 - \Sigma_j \gamma_j). \quad (30)$$

A rearrangement of the initial data matrix at every experimental step makes it possible to investigate successively the dynamics of the significance of the impact the factors have on all system indicators that become responses successively. This method increases the statistical significance of the results obtained from the algorithm for the recomputation of the initial data matrix. The algorithm embodies serial repeatability of the experiments by fixing the factors at certain levels. If the experiment is passive, the rows of the initial matrix are chosen in a special way so that, in every computation, rows with the closest values of factors (indicators) influencing the response are grouped together. The dynamics of the specific contributions is computed by using the principle of data elimination.

In the proposed way, the computation of the dynamics of the insignificant information is gradually eliminated. The value of γ does not change remarkably until the significant information is rejected. A dramatic reduction of γ is associated with a threshold with which this elimination of useful information occurs. The algorithm of this operation is an iterative γ recomputation by formula (23) and a rejection of information exceeding the threshold computed. In the algorithm, the significance of the result and of the information eliminated is increased by recomputing the initial data matrix into a series-averaged matrix, the series being, for instance, the totality of matrix rows grouped around the closest values of the factor in the case of a passive factorial experiment. The series may also consist of repeated changes of the indicator with the others fixed at a specified level. Because in further discussion the series-averaged matrix is processed in order to obtain final results, the compilation of series from the data in a field is a major task for the user because, both, the numerical and meaningful (qualitative) result of the computation may be influenced. With increasing threshold the amount of rejected information also increases, therefore one has to check whether the amount of information in the series-averaged matrix is sufficient, see below. Consequently, the information on the factor considered in this version of the method is rejected by the formula $$X_{1i}=[\Sigma_p X_{1ip}-m*h]/n_i, \; p=1,2,\ldots,m; \; i=1,2,\ldots,N,$$

where $X_{1i}$ is the value of the i-th series in which the factor $X_1$ is observed and for which the critical (rejection) threshold is determined after the elimination of data with a threshold of H; $n_i$ is the number of observations in the i-th series; m is the number of values of the $X_1$ which exceed h and ($0 \leq m \leq n_i$); N is the number of observation series (rows of the N*(K+1) matrix of the initial information, where K is the number of factors investigated simultaneously.)

The invention thus provides image searching and comparison based in a much more direct way on image content and meaning than has been previously available. In addition, using the described method of weights calculations for targeting similarities between a multi-component template and a database of images in medical fields is much more mathematically justified and sound than neural network techniques used for the same purposes. That is important to understand because template matching may be used in such applications to decrease the difficulty of database creation and search, and improve early cancer diagnostics, early melanoma detection, etc.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of retrieving one or more digital images or portions of digital images comprising:
   providing a query image;
   processing said query image with one or more filters so as to modify pixel values in said query image and to distinguish at least one set of filtered object pixels from background pixels in said query image, wherein said filters include at least one of a look-up table filter, a filter which sharpens small scale features within a distinguished object, and a shading correction filter, wherein a shape defined by said distinguished filtered object pixels depends on said filters, wherein intensity values of said filtered object pixels also depend on said filters, and wherein the visual characteristics of an object which are related to object characterization are enhanced by said filters;
   calculating a single object characterization parameter using as at least one set of inputs either (1) the intensity values of substantially all and substantially only said filtered object pixels, (2) the relative position of at least some object pixels on the perimeter of said distinguished object, or (3) the total number of distinguished object pixels;
   assigning an object characterization parameter set comprising said object characterization parameter to at least one set of said filtered object pixels in said query image;
   comparing said object characterization parameter set with one or more additional object characterization parameter sets associated with sets of object pixels defined in images in an image database or with other sets of object pixels defined within said query image; and
   selecting one or more sets of object pixels, clusters of sets of object pixels, or images in response to said comparing.

2. The method of claim 1, wherein said processing comprises filtering said filtered image pixel values with multiple additional filtering functions so as to produce subsequent sets of filtered image pixel values.

3. The method of claim 1, additionally comprising displaying said filtered image pixel values.

4. The method of claim 2, additionally comprising displaying said subsequent sets of filtered image pixel values.

5. The method of claim 1, wherein said processing comprises defining an edge around at least one of said one or more sets of object pixels.

6. The method of claim 1, additionally comprising processing all or a subset of images in said image database in a substantially identical manner to the processing performed on said query image.

7. The method of claim 1, wherein said object characterization parameter set is defined at least in part by filtered pixel brightness values within said one or more sets of object pixels.

8. The method of claim 1, wherein said object characterization parameter set comprises an ordered series of numeric parameters.

9. The method of claim 8, wherein at least a portion of said numeric parameters are representative of aspects of the visual appearance of said filtered set of object pixels to a user.

10. The method of claim 1, wherein said query image is provided to an Internet server over a communications link, and wherein said processing, assigning, and comparing are performed on said Internet server or other available Internet tools and capacities.

11. An image retrieval system comprising:
   an image database comprising a plurality of images;
   at least one query image stored in a memory;
   a filter set receiving said query image and receiving said images from said database as inputs and configured to provide a filtered query image and filtered database images as outputs, wherein said filter set includes at least one of a look-up table filter, a filter which sharpens small scale features, and a shading correction filter;

a display configured to display under user control the query image both before and after filtering by said filter set, and also to display database images both before and after filtering by said filter set;

an object definition module in data communication with said filter receiving said filtered query image and said filtered database images as inputs, and configured to define sets of object pixels within said filtered query image and said filtered database images, and wherein the definition and intensity values of at least some of said object pixels depend on the filter set and wherein characterizing features within objects are enhanced by application of said filter set;

an object parameterization module configured to calculate a parameter set associated with at least one set of object pixels in said filtered query image and a parameter set associated with at least one set of object pixels in said filtered database images, said parameter sets each including at least one parameter calculated using as at least one set of inputs either (1) the intensity values of substantially all and substantially only said filtered object pixels, (2) the relative position of at least some object pixels on the perimeter of said distinguished object, or (3) the total number of distinguished object pixels; and a parameter set comparison module receiving said parameter sets as inputs, and configured to compare the content of said parameter sets.

12. The image retrieval system of claim 11, wherein said parameter set comparison module is configured to calculate a similarity index from said parameter sets representative of content similarity between said query image and at least one image in said image database.

13. A method of analyzing digital images so as to verify a suspected biological, medical, chemical, physical or clinical condition of a patient comprising:

processing a first image of a portion of a first human body having a suspected clinical condition with a one or more filter functions so as to modify at least some pixel intensity values and so as to define at least one separated portion of said first image, wherein said separated portion comprises a first set of object pixels distinguished from background pixels, and wherein said first set of object pixels is associated with a physical structure in said first human body potentially related to said suspected biological, medical, chemical, physical or clinical condition;

parameterizing said separated portion of said first image to produce a corresponding parameter set associated with said separated portion of said first image, said parameter set including at least one parameter selected from area, perimeter, maximum diameter, minimum diameter, form factor, equivalent circular diameter, aspect ratio, optical density, integrated density, relief, and homogeneity;

processing a second image of a portion of a second human body having a known biological, medical, chemical, physical or clinical condition with substantially the same one or more filter functions so as to define at least one separated portion of said second image, wherein said separated portion comprises a second set of object pixels distinguished from background pixels, and wherein said second set of object pixels is associated with a physical structure in said second human body related to said known biological, medical, chemical, physical or clinical condition;

parameterizing said separated portion of said second image to produce a corresponding parameter set associated with said separated portion of said second image, said parameter set including at least one parameter selected from area, perimeter, maximum diameter, minimum diameter, form factor, equivalent circular diameter, aspect ratio, optical density, integrated density, relief, and homogeneity; and comparing the content of a parameter set associated with at least one separated portion of said first image with the content of a parameter set associated with at least one separated portion of said second image so as to produce a measure of similarity between the structure in the first human body having the suspected biological, medical, chemical, physical or clinical condition and the structure in the second human body having a known biological, medical, chemical, physical or clinical condition.

14. The method of claim 13, wherein said comparing comprises calculating a similarity index using the content of said parameter sets.

* * * * *